United States Patent [19]

Bunyan

[11] 4,035,483

[45] July 12, 1977

[54] ANTISEPTIC AND NON-TOXIC SUBSTANCE AND A METHOD OF MAKING THE SAME

[76] Inventor: John Bunyan, Seafield House, 19 The Beach, Walmer, Kent, England

[21] Appl. No.: 602,410

[22] Filed: Aug. 6, 1975

Related U.S. Application Data

[63] Continuation-in-part of Ser. No. 364,313, May 29, 1973, abandoned.

[51] Int. Cl.² .................. A61K 33/20; A61K 37/00
[52] U.S. Cl. .................................. 424/149; 424/177
[58] Field of Search ........................... 424/177, 149

[56] References Cited

PUBLICATIONS

Chem. Abst., vol. 10 (1916) p. 2374[b].
Chem. Abst., vol. 44 (1950) p. 5487c.
Wright – Biochem. J. vol. 20 (1926) pp. 524–532.
Benjamin et al. – Archives of Surgery, vol. 88 (1964) pp. 725–727.

*Primary Examiner*—Sam Rosen
*Attorney, Agent, or Firm*—Lawrence Rosen; E. Janet Berry

[57] ABSTRACT

A non-toxic, antimicrobial, surgically effective antiseptic material comprising the reaction product of hypochlorite and a protein is described. It is useful in treating burns and other wounds to prevent, control, and treat infection without interfering with the normal healing process. A preferred embodiment is a biological dressing comprising the antiseptic material in a film of a biologically acceptable organic substance.

30 Claims, 4 Drawing Figures

ANTISEPTIC AND NON-TOXIC SUBSTANCE AND A METHOD OF MAKING THE SAME

This application is a continuation-in-part of United States Application Ser. No. 364,313 filed May 29, 1973, now abandoned.

This invention relates to antiseptics that are surgically active. This means that they are effective in the treatment and/or prevention of surgical infections, that is to say infections in open wounds, such as surgical or accidental wounds, burns, ulcers and other lesions. A material will only be surgically active as an antiseptic if it has very powerful antiseptic properties and if it does have such powerful antiseptic properties then naturally the material may be useable in other instances, for instance in the treatment of medical infections, for example respiratory diseases, diseases of internal organs and diseases caused by moulds, and also in the sterilisation of, for example, blood.

Currently there are a large number of surgically active antiseptic materials, including antibiotic compounds, on the market to control or treat infection. However, despite this large number of materials, and although it has been recognised that many chemicals and irradiation will kill disease organisms, infection remains one of the most significant, if not the most significant, problem in medicine today. This is due to substantial part to the recognition that for a substance to perform as an antiseptic to prevent or control bacterial infection, the substance cannot be a tissue poison.

The most common antiseptic materials present in use are silver compounds such as silver sulfa-mylon, silver sulfa-diazine, and silver nitrate. Although these compounds are reasonably satisfactory for the control of infection in burns, they are of little value in most surgical conditions such as other wounds, ulcers, and abscesses. These silver compounds, although being similar in bactericidal action, exhibit varying degress of local and general toxaemia, delay the separation of the dead tissue in burns, and delay healing. Additionally, at least sulfa-mylon is often very painful and is referred to in medical circles as "the white heat". Additionally, the material is expensive. None is effective in the control of established infection. Solutions of iodine have been used as an antiseptic material especially in the treatment of open wounds and burns. Although iodine solutions are effective in controlling primary and low-grade secondary infection, they are of little value in acute and gross infection, and, furthermore, have little effect in the control of established infection. Other materials which have been suggested as antiseptics in recent years include hexachlorophene primarily as a skin decontaminant. However, hexachlorophene has limited application because of its toxicity. Although various antibiotics have been suggested for control of infection, each is less than satisfactory since, although a particular antibiotic may control or eliminate a particular type of bacteriocidal infection, other types of bacteria immuned to the particular antibiotic elected will take over and take the place of the first bacteria.

Hypochlorites are very well known to be useful in controlling the growth of micro-organisms in various environments and for various other pharmaceutical purposes. For instance, in British Patent Specification No. 1,027,978 it is proposed to form a blood plasma substitute by reacting gelatin with a hypochlorite solution at a temperature preferably between 70° and 100° C using an amount of hypochlorite that is, measured as active chlorine, 0.1 to 10% of the amount of gelatin. Thus the amount of hypochlorite measured as active chlorine is very much less than the total amount that is capable of reacting with gelatin, and instead the hypochlorite seems to be being used to result primarily in a particular type of hydrolysis of the gelatin.

In Chemical Abstracts 1950, Vol. 44, page 5487c, there is an Abstract of an article in the "Journal Dairy Research" Vol. 16, 1949, pages 327 to 333. The Abstract states the compounds formed by the interaction of hypochlorite with proteins have some germicidal power, and that these compounds act more slowly then hypochlorite. The resultant product was stated to have a definite but slow action against *streptococcus cremoris*. Reference to the full article in "Journal Dairy Research" shows that the reaction was conducted by mixing hypochlorite with glycine or skim milk using a hypochlorite concentration in eacn experiment within the range 130 to 150 parts per million. It is stated that the results showed that compounds formed by the interaction of hypochlorite with protein act as germicides more slowly than free hypochlorite and that where protein is present in excess the germicidal value of the mixture is low. This article therefore suggests that products obtained by the interaction of protein and hypochlorite solutions will have slower activity than hypochlorite but may be useful for slow control of an organism such as *streptococcus cremoris*. *Streptococcus cremoris* is, of course, an organism that is quite easily controlled and a product that is only capable of slow control of this organism can be expected to be completely useful in the prevention or control of the much more virulent organisms that are likely to be encountered in wounds, and thus such a product would be expected to be absolutely useless as a surgically active antiseptic.

Hypochlorite solutions themselves have, of course, been suggested for many pharmaceutical uses, including the treatment of burns, wounds, ulcers, and abscesses, and as an irrigating antiseptic in the genital urinary track. Although the hypclorites have been successful and are a useful medicinal tool, a primary disadvantage in their use is the need for large quantities of a dilute solution to produce the required results. Concentrations above about 0.1% are too painful for general use. Accordingly, the use of hypochlorites requires special application techniques requiring time and nursing skill. As a result they are not widely used as surgically active antiseptics.

Accordingly, it is a primary object of the present invention to provide a novel and non-toxic antiseptic for use in the treatment, control and/or prevention of surgical and/or medicinal infection.

Another object of this invention is to provide a novel and non-toxic substance which is bactericidal, non-irritating to skin or wounds, and which does not delay the healing process.

Another object of this invention is to provide a novel, antiseptic, and non-toxic substance which is bactericidal and which is painless upon application to burns and other open wounds.

It is another object of this invention to incorporate a novel, non-toxic, antiseptic, and antimicrobial substance which will release antimicrobial and antiseptic material in controlled amounts.

It is another object of this invention to provide a novel and non-toxic antiseptic substance in bandage form which is inexpensive, painless, reduces edema, and does not interfere with the normal healing process.

It is another object of this invention to provide a novel, antiseptic, and antimicrobial substance in bandage form which is bactericidal, anti-inflammatory, non-toxic, and has no unpleasant odor or taste.

Another object of this invention is to provide an antiseptic and antimicrobial substance in bandage form which has controlled and sustained release of active material.

These and other objects of the present invention will be more readily apparent from the following detailed description with reference to the accompanying drawing.

I have now found that a composition that is a surgically active antiseptic, and that is therefore effective in controlling or preventing infection in wounds, comprises a surgically active concentration of the reaction product obtained by mixing together a protein and a substantially stoichiometric amount of an aqueous solution of a hypochlorite.

If the concentration of reaction product is too dilute then of course the activity of the product will be reduced to such an extent that it can no longer be considered to be surgically active. A product in which the amount of hypochlorite is initially as low as 150 p.p.m. (as in the aforesaid Journal of Dairy Research article by G.A. Cox and H.R. Whitehead) is much too dilute to be surgically active.

In its simplest embodiment the composition is made merely by mixing together the protein and the aqueous solution and utilising the resultant solution as the antiseptic composition. If the amount of hypochlorite is too low then the concentration of the reaction product in the solution will be too low for the composition to be surgically active, and generally surgical activity can be considered to start when the concentration of hypochlorite used in the reaction mixture is at least 0.5%, measured as active chlorine. Preferably the reaction is conducted using a more concentrated hypochlorite solution and most preferably a solution having the maximum commercially available hypochlorite concentration, for instance about 5.25% measured as active chlorine, is used. If this is the concentration of active chlorine present in the reaction mixture that produces the reaction product, then it will be seen that the resultant product can be diluted with water by an amount of up to 10 to 12 times the amount of the reaction product and still maintain the surgical effectiveness of the composition. However, if the reaction mixture has a lower hypochlorite concentration then clearly the amount of dilution that is permitted in forming the antiseptic composition will be correspondingly less.

If desired hypochlorite solutions having a concentration greater than the commercially available 5.25% solution can also be used.

It is generally desirable to ensure that all the hypochlorite solution is reduced, that is to say is reacted with the protein. Further, it is generally desirable that sufficient hypochlorite is used to complete reaction, that is to say to react completely with the protein. Accordingly substantially stoichiometric amounts of hypochlorite and protein should be used. If too much hypochlorite is used so that the final reaction product contains free hypochlorite solution, then the product is liable to suffer from the disadvantages, and in particularly the pain, associated with hypochlorite solutions in general. If too much protein is used it is wasteful, no advantages are gained, and the effectiveness of the product may be reduced. Preferably the amount of protein is not greater than 10% above that required for complete neutralisation of the hypochlorite.

Depending upon the reaction conditions and materials used, the reaction product may be a solution and or a mixture of a solution and a deposit, and both are surgically active antiseptics. Generally, however, it is preferred to utilise the solution.

The surgically active antiseptic compositions of the invention may consist solely of the reaction product, for instance consisting essentially of a powder made by, for instance, lyophilisation of the solution or by drying of the deposit mentioned above, or may comprise the reaction product and a pharmaceutically acceptable carrier. This carrier may be water, for example the water of the reaction mixture in which the reaction product was formed and/or additional water used to dilute the reaction product if the hypoclorite solution was initially sufficiently concentrated to permit this while retaining a surgically active concentration, or any other suitable pharmaceutical carrier.

A particularly preferred composition is one comprising the reaction product impregnated in or coated on a sheet carrier. Such a composition may be wet, for example being in the form of a swab comprising lint or other fibrous or sponge material saturated with a solution of the composition, or may be dry. In dry dressings the carrier can be a film, a sponge, or a textile, for example a woven, non-woven or knitted textile, or paper. If it is a film then the film may be reinforced by fibrous material, for example a woven or non-woven textile. Dressings in which the carrier is a film are conveniently made by impregnating a fibrous or other reinforcement with a film-forming solution comprising the reaction product and a suitable film-forming component or by casting a film-forming solution comprising the reaction product and a suitable film-forming component. As film-forming component there may be used any material that is compatible with the reaction product and which is capable of forming a film upon impregnation or casting in the described manner. Typical film-forming components are naturally occurring or modified polymers such as cellulose derivatives, for instance carboxymethyl cellulose of hydroxyethyl cellulose and synthetic polymers, for instance polyvinyl alcohol. Knitted, non-woven or woven textiles can be used as the carrier and can be any of those conventionally used for protective dressings, and conveniently are impregnated with a solution of the reaction product and are then dried. Any dry dressings according to the invention conveniently can be attached to a suitable backing that carries an adhesive on the outer portions at least of the surface to which it is attached, so as to facilitate fixing of the dressing in position, in the usual manner for protective dressings of small external wounds.

Although the surgically active antiseptic compositions of the invention can be used for, for instance, sterilising stored blood or treating medical infections, such as respiratory diseases, they are of particular value for the prevention or control of infections in external wounds, especially burns but including also other wounds and ulcers and other lesions.

The novel composition can be applied to the burn or other wound as a solution, for example being washed over the wound, sprayed onto the wound or applied by a swab or sponge. It may be formulated appropriately, for example as an aerosol, to permit spraying. It can also be formulated as an ointment or cream, with a suitable base. It may also be applied to the wound as a dry composition, for example as a powder consisting or comprising of the reaction product or as a dressing comprising the reaction product impregnated in or coated on a sheet carrier. However it is applied it is found that the composition is a surgically active antiseptic, and thus controls and usually prevents infection in the burn or other wound and is wholly non-toxic. Thus so far as I am able to determine the compositions of the invention have no deleterious effect on healing tissue, they do not prevent blood clots from organising, and they cause no pain, even when applied to a fresh burn or other wound. This is particularly surprising since the maximum concentration of hypochlorite which can be utilised in practice is about 0.1% active chlorine, any greater concentration being too painful for general application, whereas in the invention the amount of hypochlorite in the reaction product must always be greater than about 0.5%, measured as active chlorine. Further, the compositions of the invention are anti-inflammatory and have no unpleasant odor or taste. They appear to exert both bactericidal and fungicidal effects. They are inexpensive to produce and are chemically stable.

To demonstrate the effectiveness and painlessness of the compositions a human volunteer was submitted to a 4 centimeter third-degree burn and was treated with the antiseptic composition of the invention throughout the entire healing process. The healing occurred satisfactorily and the volunteer felt no pain during the healing.

The proteins used for forming the reaction product are preferably animal or vegetable proteins, although synthetic proteins can be used. Preferred animal or vegetable proteins include (1) human or animal skin tissue, subcutaneous tissue, muscle or bone tissue; (2) whole blood, blood serum, fibrin, or organs; (3) egg albumin, egg yolk, or a combination of albumin and yolk; (4) gelatin; (5) vegetable proteins obtained from plants such as nuts or beans. Of these animal tissue, blood serum and gelatin are preferred. Human serum albumin may be preferred as the blood serum, but bovine serum is generally a satisfactory alternative. For cost reasons gelatin will naturally be preferred.

The hypochlorite solution can be a solution for any hypochlorite, including a solution formed by dissolving hypochlorous gas in water. Usually, however, it is a solution of an alkaline earth hypochlorite, for example calcium hypochlorite or of hypochlorous acid itself or, preferably, of an alkali metal hypochlorite, preferably sodium or lithium hypochlorite.

The reaction is best conducted simply by mixing the protein and the hypochlorite solution. The mixing may be conducted with agitation if desired. Although higher temperatures can be used, it is generally preferred to conduct the reaction at temperatures of 80° F and lower. The optimum temperature for any particular reaction will depend upon the particular protein being used. For instance, when the protein is gelatin the optimum is generally between 40° and 80° F, preferably between 40° and 60° F. At lower temperatures there is a tendency for an increasing amount of deposit to result from the reaction and, as mentioned above, it is generally more convenient to use the solution that is formed. With blood serum the optimum reaction temperature is generally below 60° F, e.g. between 2° and 60° F.

The dry protective dressings comprising the reaction product and which are described are extremely useful as protective dressing for burns and other wounds in that they act as surgically active intiseptics for the wounds and healing of the wounds is facilitated.

A particularly serious problem confronting physicians concerned with treating large wounds, for instance on patients that have been seriously burned, is the lack of availability of suitable biological dressings, that is to say dressing that can be positioned over the wound and can grow into the wound during the healing process. Although various biological dressings have been proposed none are satifactory in practice, with the result that skin grafting is generally the only satisfactory way of repairing extensive wounds. However, with a seriously burned patient even this may not be possible. A biological dressing based on animal skin can be used in some instances, but there are serious problems in maintaining it sterile while the tissue grows around it, and similarly although gelatin could in theory form the basis for a biological dressing in practice it cannot, again because of the problem of microbiological contamination which occurs quickly in such a dressing even when it is protected by any of the antiseptics that are commercially and conveniently available.

Accordingly there is an urgent need to provide a dressing that is both a biological dressing and is a surgically active antiseptic. It is a further object of the invention to produce such a dressing.

A biological, surgically effective antiseptic, dressing according to the invention comprises a film of a film-forming biologically acceptable organic substance and a reaction product of an aqueous solution of hypochlorite with at least a substantially stoichiometric amount of protein.

The biologically acceptable organic substance is itself usually proteinaceous, and so there are generally two convenient ways of making the film. In one method the film-forming subtance either in the form of a film or in the form of a liquid, e.g. colloidal suspension, that can be made into a film, is combined with a pre-formed reaction product of an aqueous solution of hypochlorite with a substantially stoichiometric amount of the protein. The reaction product may be made using the reactants and concentrations and reaction conditions as described above. Thus, for instance, a reaction product as described above may be mixed in an aqueous medium, part at least of which is generally provided by using the reaction product in the form of the aqueous solution in which it is initially made, with a solution or dispersion, e.g. a colloidal dispersion, of the film-forming substance, and after mixing the mixture is formed into a film, e.g. by casting or by impregnating a fibrous reinforcement, and if necessary drying the film.

If the biological dressing is made by combining a reaction product with a pre-formed film, then conveniently this is done by contacting the reaction product in the form of an aqueous solution with the pre-formed of film-forming substance. For instance pig or other animal skin, or human skin that is being prepared for a skin graft, can be soaked in or sprayed with the reaction product in the form of an aqueous solution.

In the second method of making the biological dressings the aqueous solution of hypoclorite is reacted with greater than a substantially stoichiometric amount of a protein that is a biologically acceptable film-forming substance. Although the reaction of hypochlorite with most film-forming proteins, such as gelatin, destroys their film-forming capacity, if a greater than substantially stoichiometric amount of protein is used not all of the protein will react with the hypochlorite with the result that the final product will be a mixture of film-forming protein and protein that has reacted with hypochlorite, and thus the product can exist in film form.

Reaction temperatures and hypochlorite solutions used in these processes may be all as described above.

The film-forming substance can be any biologically acceptable organic substance that is capable of coalescing with the healing tissue that forms during the healing of a wound. Suitable materials include fibrin, collagen, gelatin, alginate and human or animal skin, e.g. pig skin. Gelatin is often preferred. The protein with which the hypochlorite is reacted in the biological dressing may be any of these materials or it may be a non-film-forming protein, in which event of course the dressing has to be made by combining a reaction product of hypochlorite and a non-film-forming protein with the film-forming protein. Any of the non-film-forming animal or vegetable proteins mentioned above may be used, for instance blood serum.

As with all antiseptic products of the invention it is necessary that the dilution of protein that has reacted with hypochlorite in the product shall not be too great. Thus as described above the concentration of hypochlorite in the reaction medium must be at least 0.5% by weight, and conveniently the solution used is as described above, namely a 5.25% solution. The amount of film-forming material in the biological dressing should not be more than at the most 20, and preferably not more than 10, times the weight of the stoichiometric amount of protein required to react with all the hypochlorite, as otherwise the degree of dilution of the antiseptic reaction product by the film-forming proteinaceous material may be too great for the product to function as a surgically effective antiseptic film. Thus if the dressing is made by forming a reaction product and then combining it with film-forming substance, the amount of film-forming substance used should not be more than 20, and preferably not more than 10, times the weight of protein used for forming the reaction product. The minimum amount of film-forming substance that has to be present in the dressing is generally the same weight as the amount of protein that reacts with the hypochlorite. Thus if the dressing is made by combining the reaction product with film-forming substance, the weight of film-forming substance should be at least as great as the weigh of protein used for forming the reaction product. Alternatively the dressing can be made by reacting hypochlorite with at least twice the substantially stoichiometric amount of film-forming protein, but with not more than 10, or at most 20, times the stoichiometric amount.

The biological dressing may consist solely of the film-forming material and the reaction product, but often includes a fibrous reinforcement, the film then being obtained by, for instance, impregnating an aqueous system containing a solution or dispersion of the film-forming material and the reaction product in a fibrous carrier, such as gauze, lint, paper towelling or the like. It is naturally desirable that the impregnation should be carried out in such a way that the film-forming material, and not the fibrous reinforcement, comes into direct contact with the wound in order that the fibrous reinforcement does not interfere with the participation of the film-forming material and the reaction product in the healing process, and in particular with the coalescence of the film-forming material and the reaction product with the underlying tissue that appears to occur during healing.

Naturally the film of film-forming material and reaction product, optionally including a fibrous reinforcement, may be provided with a suitable backing, generally a fibrous backing, in conventional manner as described above.

Although it appears to coalesce with the underlying tissue, it has been established that the film has no deleterious affect from the standpoint of the natural healing of the wound, or drainage. Drainage occurs apparently due to the proteolytic action of any products of suppuration on gelatin or other film-forming material. The dressings are painless in application, prevent infection, reduce edema, and do not interfere with the normal healing process. Moreover, the material, due to the presence of the reaction product, has bactericidal and anti-inflammatory properties and no unpleasant odor. The reaction product is released in a controlled amount from the carrier over a sustained period of time.

If the dressing does not consist of a biologically acceptable material (for instance if it includes additional fibrous reinforcement) then it will be necessary to remove this reinforcement at least after healing. It is found that as a result of choosing water soluble film-forming substances removal of the dressing from the wound after healing is easily effected merely by washing. Thus if a film that has a fibrous reinforcement in it on one side is applied to a wound with the reinforcement distant from the wound, after healing the reinforcement and the remnants of the film can be washed off the wound.

Having described the invention in general terms, the following Examples will provide preferred embodiments of the invention.

EXAMPLE 1

65 cc. of 5.25 percent sodium hypochlorite (NaOCl) is titrated with 5 cc. of blood serum at about 40° F until all liberation of gases ceases. Two drops of serum are then added to ensure that all hypochlorite has been neutralised. The solution is stirred during reaction. The solution is filtered, and the filtrate used as an antiseptic.

EXAMPLE 2

65 cc. of 5.25 percent lithium hypochlorite (LiOCl) is stirred with 1 g. of animal tissue until the tissue is dissolved. The solution is filtered and the filtrate retained.

EXAMPLE 3

65 cc. of 5.25 percent sodium hypochlorite (NaOCl) is admixed with 1 g. of mixed egg albumin and yolk. During thorough mixing, the mixture coagulates. The coagulant is used as an antiseptic.

EXAMPLE 4

65 cc. of 5.25 percent sodium hypochlorite (NaOCl) is reacted at about 60° F with sufficient gelatin to completely neutralise the hypochlorite, the end point being determined by the cessation of gas evolution. A solution is formed, with no precipitate, and is used as an antiseptic.

EXAMPLE 5

Sufficient gelatin is added to the solution obtained in Example 4 to provide, on a weight basis, 5 parts of gelatin and 1 part of the solution. The mixture is impregnated into a gauze material and allowed to dry, thereby forming a reinforced biological dressing.

EXAMPLE 6

A biological dressing is made by admixing 1 part by weight of the solution of Example 1 with 6 parts by weight of gelatin with stirring. The gel which is formed is then formed into a film having a thickness of approximately 1/16th of an inch. The film when allowed to dry is a coherent, substantially uniform film.

EXAMPLE 7

In a manner similar to that given in Example 5 the 5 parts of gelatin may be replaced by the same amount of fibrin, collagen or alginate that is dispersed in the solution obtained from Example 4.

EXAMPLE 8

A biological dressing is made by admixing 20 cc. of a 5.25 percent sodium hypochlorite solution at 60° C with 5 grams gelatin. After gas evolution had ceased the product was cast as a film which was allowed to dry.

EXAMPLE 9

A biological dressing may be made by soaking or spraying a film of pig skin or human skin or other preformed film of biologically acceptable film-forming substance with the solution obtained in Example 4.

Biological dressings of the invention are illustrated in the drawing wherein.

Figure 1:
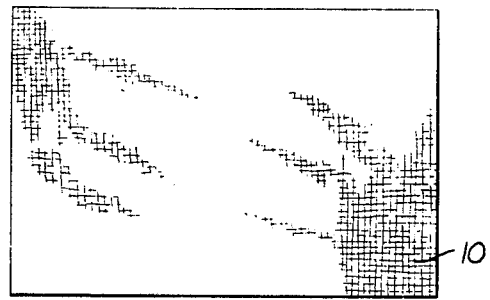
FIG. 1 is a plan view of a gauze carrier material 10 uniformly impregnated with the Example 5 material 12 which after drying fully fills the interstices of the gauze carrier.
Figure 2:
FIG. 2 is a cross-section of the dressing of FIG. 1.
Figure 3:
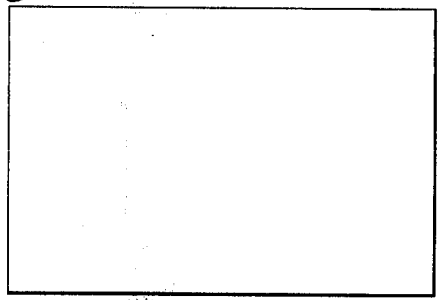
FIG. 3 is a plane view of the dressing formed in Example 6.
Figure 4:
FIG. 4 is a cross-section of the dressing of FIG. 3.

In the above Examples, the hypochlorite can be employed in varying concentrations down to as low as 0.5 percent. Additionally, the proteinaceous material can be replaced with any proteinaceous material which will completely neutralise a hypochlorite solution having a concentration of at least 0.5 percent. Moreover, in the aforesaid Examples, although sodium and lithium hypochlorite have been employed, other hypochlorites can be utilised, such as salts of calcium and potassium. Any reaction temperature, preferably below 80° C, can be used.

The solution obtained in Examples 1 – 4 is a clear solution and preferably has a pH of approximately 7. If the pH is below 7, it can be suitably adjusted by the addition of an alkaline material. However, for some applications it may be preferred that the pH is somewhat above or somewhat below 7. In such instances, the pH of the solution can be suitably adjusted.

Biological and protective dressings according to the invention can be packaged in conventional manner. Depending upon the ultimate use biological dressings, for example based on gelatin as the film-forming material, may be packaged containing sufficient water that it is in a flexible form ready for use or it may be packaged so dry that it is rather brittle and will then advantageously be softened by contact with moisture before being applied to the wound. A biological dressing is normally packaged in a sterile moisture-impermeable package in conventional manner.

To establish the antiseptic, anti-bacterial, and antimicrobial characteristics of the antiseptic of the invention, hereinafter called "Chlorostat", when used as a solution or in dressing form, data is provided as follows:

Chlorastat Stability

An open beaker of Chlorastat made from human serum albumin and hypochlorite substantially as shown in Example 1 stood on the bench for 12 weeks in a temperature of 70° F. and exposed continuously to fluorescent lights. The Chlorastat had evaporated to half its original volume and sodium chloride had crystallized out. An equal amount of tap water was added to restore it to its original volume.

Bacterial (Pseudomonas aeruginosa and Staphylococcus aureus) susceptibility to this solution was tested by the broth dilution method. Results of no growth at 1:16 dilution were obtained.

Chlorstat Inhibits Growth of Micro-Organisms

Candida albicans was seeded by cotton swab moistened with broth dilution of organism onto surface of 2 percent glucose - 1 percent peptone agar plates.

Chlorstat was prepared as serial 2 fold dilns in pH 6.7 saline solution.

0.05 ml each diln dropped onto seeded plates. Plates were incubated 24 hours at 37° C.

Growth inhibition zones by Chlorastat dilutions were as follows:

| Chlorastat ml/drop | undil | 2 | 4 | 8 | 16 | dilution ratio |
|---|---|---|---|---|---|---|
| 0.05 | 27 | 25 | 17 | 0 | 0 | mm inhibition |

Chlorastat Action on Representative Gram + and Gram - Organisms

Saturated disc assay of Candida albicans and of Clinical Laboratory isolates of Staphlococcus aureus, Proteus sp., and Pseudomonas aeruginosa.

Suspensions of organisms surface seeded onto blood agar base.

Chlorastat prepared as 2 fold saline dilns. 0.025 ml diln per disc. Incubated 18 hours at 37° C.

| Organism | Chlorastat ml/disc | undil | 2 | 4 | 8 | 16 | 32 | 64 | dilution ratio |
|---|---|---|---|---|---|---|---|---|---|
| C. albicans | 0.025 | 11 | 9 | 9 | 8 | 0 | 0 | 0 | mm inhibition |
| S. aureus | 0.025 | 13 | 11 | 10 | 8 | 0 | 0 | 0 | mm inhibition |
| Proteus sp | 0.025 | 15 | 13 | 12 | 8 | 7* | 0 | 0 | mm inhibition |
| Ps. aerugin osa | 0.025 | 12 | 11 | 10 | 0 | 0 | 0 | 0 | mm inhibition |

*slight growth only

Chlorastat Activity in Presence of Serum And of Whole Blood

Disc assay of organism suspensions surface seeded onto 6 percent blood agar, or onto blood agar base. Chlorastat serial 2 fold dilns prepared in serum, in whole blood, and in saline. 0.025 ml/disc. Incubated for 18 hours at 37° C.

| Chlorastat diluent | Chlorastat ml/disc | Plating medium | organism | undil | 2 | 4 | 8 | diluent control dilution ratio |
|---|---|---|---|---|---|---|---|---|
| saline | 0.025 | blood agar | C. albicans | 10 | 8 | 0 | 0 | 0 mm inhibition |
|  |  |  | Proteus sp | 14 | 11 | 9 | 8 | 0 mm inhibition |
| serum | 0.025 | BAB | C. albicans |  | 0 | 0 | 0 | 0 mm inhibition |
|  |  |  | Proteus sp |  | 11 | 8 | 0 | 0 mm inhibition |
| whole blood | 0.025 | BAB | C. albicans |  | 0 | 0 | 0 | 0 mm inhibition |
|  |  |  | Proteus sp |  | 0 | 0 | 0 | 0 mm inhibition |

Comparison of Chlorastat With Other Burn Compounds

Method-seeded agar with 18 mm dia wells containing dressings or compounds. Incubation for 24 hours at 37° C. in trypticase soy dextrose agar (BBL).

| Results: agent/amount | | Zones of inhibition in mm (well dia 18 mm) dia of plate 150 mm | | |
|---|---|---|---|---|
| | | Pseudomonas aeruginosa | Mucor sp. (mold) | Candida Albicans |
| Chlorastat | 0.5 ml | 24 | 28 | 40 |
| Chlorastat dressing | 25 cm$^2$ | −* | −* | 31 |
| Silver sulfa | 2 gm | 30 Retarded | 26 (34 Retarded) | 20 |
| Sulfamylon | 2 gm | 31 | 28 Retarded | 22 |

*no growth directly under dressing

The data set forth above while being directed primarily to Chlorastat per se is also generally applicable to the Chlorastat dressing. The present specification described in general terms and detailed embodiments Chlorastat solutions and Chlorastat dressings. One skilled in the art based on the general description and disclosure of the specific examples will be able to practice the invention without difficulty.

Throughout the specification I refer to the reaction obtained by mixing a protein and a hypochlorite and to the substantially stoichiometric amount of reactant required for this. It will be appreciated from, for instance, the foregoing Examples that the reaction is preferably conducted at ambient temperatures and the stoichiometric amount of hypochlorite is that which is required to react with all the protein at ambient temperature with the liberation of gas. Accordingly, as indicated in Example 1, the amount can conveniently be determined by adding hypochlorite until there is a slight excess of hypochlorite in the mixture as indicated by the cessation of gas liberation and then adding a small amount of protein to remove the excess.

However, as will be readily appreciated by one skilled in the art, various modifications can be made to the specific Examples which fall within the general scope of the inventive concept and within the scope of the appended claims.

I claim:

1. A surgically active antiseptic composition, effective in controlling or preventing infection in wounds, and comprising a surgically active antiseptic concentration of the reaction product obtained by mixing together a protein and a substantially stoichiometric amount of an aqueous solution of a hypochlorite.

2. A composition according to claim 1 in the form of a powder consisting essentially of the said reaction product.

3. A composition according to claim 1 comprising the said reaction product and a pharmaceutically acceptable carrier.

4. A composition according to claim 1 comprising an aqueous solution of the said reaction product.

5. A composition according to claim 1 in the form of a dressing comprising the reaction product impregnated in or coated on a sheet carrier.

6. A composition according to claim 1 in which the hypochlorite is selected from sodium or lithium hypochlorites.

7. A composition according to claim 1 in which the hypochlorite is selected from sodium or lithium hypochlorite aqueous solutions having a concentration substantially of 5.25% measured as active chlorine.

8. A composition according to claim 1 in which the protein is selected from animal or vegetable proteins.

9. A composition according to claim 1 in which the protein is selected from animal tissue, blood sera or gelatin.

10. A composition according to claim 1 in which the protein is gelatin.

11. A method of preventing or controlling infection in an external wound comprising treating the wound with a composition comprising a surgically active antiseptic concentration of the reaction product obtained by mixing together a protein and a substantially stoichiometric amount of an aqueous solution of a hypochlorite.

12. A method according to claim 11 comprising treating the wound with an aqueous solution comprising a surgically active antiseptic concentration of the said reaction product.

13. A method according to claim 11 comprising applying over the wound a sheet carrier that has on the surface in contact with the wound, or is impregnated with, a surgically active antiseptic concentration of the said reaction product.

14. A biological dressing that is a surgically effective antiseptic and that comprises a film of a biologically acceptable film-forming substance and a surgically active antiseptic concentration of the reaction product of an aqueous solution of hypochlorite with at least a substantially stoichiometric amount of protein.

15. A dressing according to claim 14 in which the biologically acceptable film-forming substance is a proteinaceous material.

16. A dressing according to claim 14 in which the biologically acceptable film-forming substance is selected from fibrin, collagen, gelatin, alginate or animal skin.

17. A dressing according to claim 14 in which the protein with which the hypochlorite is reacted is a film-forming protein.

18. A dressing according to claim 14 in which the film-forming substance and the protein with which the hypochlorite is reacted are the same protein.

19. A dressing according to claim 14 made by reacting hypochlorite with from 2 to 10 times by weight the stoichiometric amount of a film-forming protein.

20. A dressing according to claim 14 made by combining a surgically active antiseptic concentration of a reaction product made by mixing together a protein and a substantially stoichiometric amount of an aqueous solution of a hypochlorite with the biologically acceptable film-forming substance.

21. A dressing according to claim 14 in which the weight of biologically acceptable film-forming substance is from 1 to 10 times the weight of protein that has reacted with hypochlorite.

22. A dressing according to claim 14 in which the protein is gelatin.

23. A dressing according to claim 14 in which the film-forming substance is gelatin.

24. A dressing according to claim 14 in which the film includes a fibrous reinforcement.

25. A dressing according to claim 14 including also a fibrous backing for the film.

26. A method of making a surgically active antiseptic comprising reacting substantially stoichiometric amounts of a protein and an aqueous solution of a hypochlorite, the amount of hypochlorite in the reaction mixture being above 0.5 percent measured as active chlorine, to obtain a reaction product having a surgically active antiseptic concentration.

27. A method according to claim 26 conducted at a temperature below 80° F.

28. A method according to claim 26 in which the protein is gelatin, and the hypochlorite solution is a solution of sodium or lithium hypochlorite.

29. A method according to claim 26 with the additional step of incorporating the product with a sheet carrier to form a dressing.

30. A method of making a biological dressing comprising reacting a hypochlorite solution of greater than 0.5% concentration with at least twice the stoichiometric amount of a proteinaceous film-forming material or combining a reaction product made by reacting substantially stoichiometric amounts of a protein and an aqueous solution of hypochlorite in a solution greater than 0.5% and combining the reaction product, in a surgically active antiseptic concentration, with a film-forming biologically acceptable organic substance.

* * * * *